US010959973B2

(12) United States Patent
Morgan et al.

(10) Patent No.: US 10,959,973 B2
(45) Date of Patent: Mar. 30, 2021

(54) COMPOSITIONS AND USES AND METHODS RELATING THERETO

(71) Applicant: The University of Manchester, Manchester (GB)

(72) Inventors: Philip Morgan, Manchester (GB); Carole Maldonado-Codina, Manchester (GB); Michael Read, Manchester (GB); Curtis Dobson, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 16/061,606

(22) PCT Filed: Dec. 14, 2016

(86) PCT No.: PCT/GB2016/053932
§ 371 (c)(1),
(2) Date: Jun. 12, 2018

(87) PCT Pub. No.: WO2017/103583
PCT Pub. Date: Jun. 22, 2017

(65) Prior Publication Data
US 2018/0369184 A1 Dec. 27, 2018

(30) Foreign Application Priority Data
Dec. 15, 2015 (GB) .................................... 1522144

(51) Int. Cl.
*A61K 31/23* (2006.01)
*A61K 9/00* (2006.01)
*A61K 47/44* (2017.01)
*A61K 36/736* (2006.01)
*A61K 8/92* (2006.01)
*A61K 9/06* (2006.01)
*A61K 36/185* (2006.01)
*A61Q 19/00* (2006.01)
*A61K 8/9789* (2017.01)
*A61P 27/02* (2006.01)

(52) U.S. Cl.
CPC .............. *A61K 31/23* (2013.01); *A61K 8/922* (2013.01); *A61K 8/9789* (2017.08); *A61K 9/0048* (2013.01); *A61K 9/06* (2013.01); *A61K 36/185* (2013.01); *A61K 36/736* (2013.01); *A61K 47/44* (2013.01); *A61P 27/02* (2018.01); *A61Q 19/005* (2013.01); *A61K 2800/87* (2013.01)

(58) Field of Classification Search
CPC ....... A61Q 19/005; A61P 27/02; A61K 31/23; A61K 9/0048; A61K 47/44; A61K 36/736; A61K 8/922; A61K 9/06; A61K 36/185; A61K 8/9789; A61K 2800/87
See application file for complete search history.

(56) References Cited

U.S. PATENT DOCUMENTS

| 4,360,387 A * | 11/1982 | Brown ................... A61K 8/922 106/243 |
| 4,866,049 A | 9/1989 | Maumenee et al. |
| 2006/0165645 A1* | 7/2006 | Lebok ..................... A61K 8/922 424/74 |
| 2011/0124725 A1* | 5/2011 | Maskin ................ A61K 31/167 514/529 |

FOREIGN PATENT DOCUMENTS

| DE | 102010026696 A1 | 1/2012 | |
| EP | 0535545 A1 | 4/1993 | |
| WO | 2005067892 A1 | 7/2005 | |
| WO | 2014191969 A1 | 12/2014 | |
| WO | WO-2015083174 A1 * | 6/2015 | ............. A61K 8/345 |
| WO | 2017103583 A1 | 6/2017 | |

OTHER PUBLICATIONS

International Search Report and Written Opinion of PCT/GB2016/053932, dated Mar. 24, 2017, 9 Pages.
Search Report of GB1522144.3, dated Sep. 30, 2016, 4 Pages.
Blackie et al., The Relationship Between Dry Eye Symptoms and Lipid Layer Thickness, 2009, Cornea, vol. 28(7), pp. 789-794.
Richard Hector, Dry Eyes and Eyelids, 2013, The Eye Associates.
Tiuseco et al., Petroleum Jelly Versus Tea Tree Oil and Tea Tree Facial Wash Lid Scrub in Patients with Blepharitis Associated with Above-normal Demodex Count, 2012, Philippine Journal of Ophthalmology, vol. 37, pp. 73-82.
Emma Reynolds, Jennifer Aniston's £1 beauty secret: Actress smooths Vaseline under her eyes to look flawless at 43, 2012, Mail Online.
Safety Data Sheet, 2015, Sigma-Aldrich.
Cosmetic Safety Consultants Ltd., Balms and Salves, 2012.
Rhoda Peacher, How to Make Beeswax Salve, 2013.
Fran Mac, How to Make Traditional Salves and Balms, 2015.
Lucinda Warner, How to Make Salves, Ointments and Balms, 2011.

* cited by examiner

*Primary Examiner* — Sean M Basquill
(74) *Attorney, Agent, or Firm* — Nixon Peabody LLP; Linda B. Huber

(57) ABSTRACT

A method for delivering a benefit agent to the surface of the eye, the method comprising applying an ocular benefit composition to a lid margin of the eye wherein the ocular benefit composition comprises at least 5 wt % of one or more lipid and/or lipid derived compounds.

6 Claims, 9 Drawing Sheets

COMPOSITIONS AND USES AND METHODS RELATING THERETO

CROSS-REFERENCE TO RELATED APPLICATIONS

This application is a National Phase of International Application No. PCT/GB2016/053932 filed Dec. 14, 2016, currently pending, which designated the U.S. and that International Application was published under PCT Article 21(2) in English. This application also includes a claim of priority under 35 U.S.C. § 119(a) and § 365(b) to British patent application No. GB 1522144.3 filed Dec. 15, 2015, the entirety of which is hereby incorporated by reference.

The present invention relates to compositions for the treatment of the surface of the eye and to uses and methods relating thereto. In particular the invention relates to a novel means for treating ocular discomfort caused by conditions such as dry eye, to means for delivering a medicament to the eye and to cosmetic compositions for the eye.

The eye is a very complex and sensitive organ. The surface of the eye is covered with a tear film which is replenished on blinking. The tear film is about 3 microns thick and is predominantly aqueous. There is an inner mucous layer and the outermost layer is a lipid layer of about 100 nm thickness. This lipid layer is very important as it prevents evaporation, and lubricates the eyelid.

The lipids are mainly derived from the meibomian glands of the eyelid which are located in the tarsal plate of both the upper and lower eyelids. Each gland opens onto the lid margin at the mucocutaneous junction. Compression of these glands during blinking results in a small amount of the lipid-containing meibum being squeezed onto the lid margin which is then incorporated into the tear film during blinking. In this way, a constant flow of these lipids find their way into the tear film in the normal eye.

However the lipid layer can in some instances become disrupted. This can lead to evaporation of the tear film and cause symptoms of dry eye.

'Dry eye' is an umbrella term used to describe a widespread ocular condition whereby a range of deficits to the tear film leads to uncomfortable eyes which can range from minor itching to significant pain (which can lead to sufferers being unable to leave their homes).

People suffering from dry eye have feelings of dryness, grittiness or soreness that worsen throughout the day. Their eyes may be red and they may experience blurred vision. Their eyelids may stick together when they wake up. In some cases they have watering eyes.

Whilst mostly an uncomfortable condition, in serious cases sufferers may experience extreme sensitivity to light, significant pain and a permanent deterioration in vision.

Dry eye is a relatively common condition, occurring more frequently in older people and most often in women.

There are a number of treatments currently available to relieve the symptoms of dry eye but none of these is satisfactory. Eye drops and ointments are available over the counter or via medical prescription. However drops can be difficult to apply and provide only very short term relief. Ointments are viscous and greasy. They tend to smear and it is difficult to see after they have been applied making them suitable only for use at night time.

More recently a spray has become available. This predominantly aqueous composition comprising a lipid emulsion is sprayed onto the eyelids when closed. However much of the active ingredient is wasted and the product leaves an unpleasant stickiness on the face. Its effect may also be short term.

There are many other conditions which affect the eye and can cause a wide variety of symptoms from mild discomfort to severe pain and vision problems. In some cases it would be advantageous to treat such conditions by topical application of an agent and/or medicament to the surface of the eye but existing means for doing this are not always desirable and/or effective.

There are also cosmetic reasons why people would like to deliver an agent to the surface of the eye.

The present invention seeks to provide improved compositions, uses and methods for delivering a benefit agent to the surface of the eye.

DETAILED DESCRIPTION OF THE INVENTION

Figure 1:
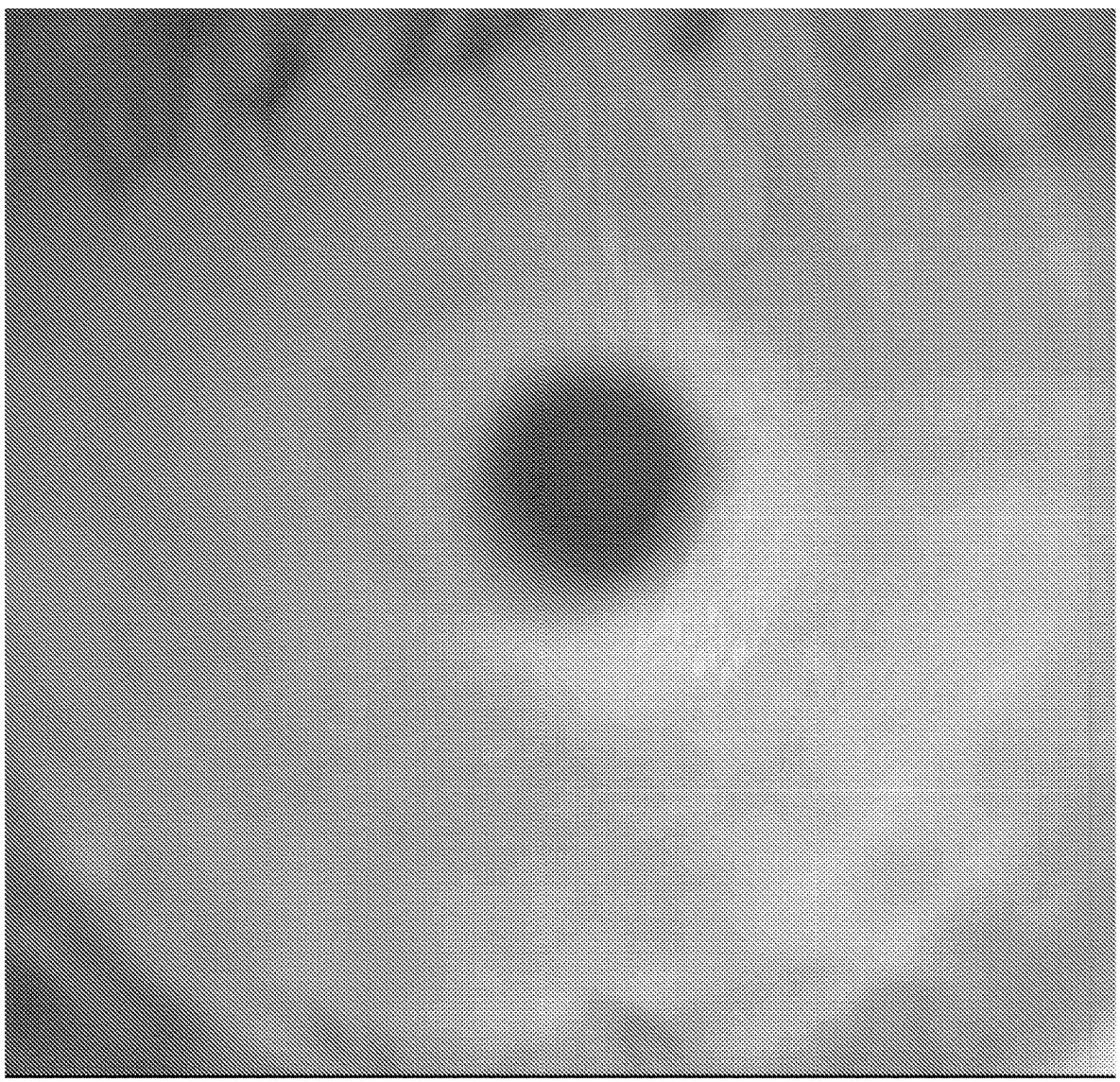
FIG. 1 shows the untreated eye at 16 x magnification.

According to a first aspect of the present invention there is provided a method for delivering a benefit agent to the surface of the eye, the method comprising applying an ocular benefit composition to a lid margin of the eye wherein the ocular benefit composition comprises at least 5 wt % of one or more lipid and/or lipid-derived compounds.

According to a second aspect of the present invention there is provided the use of an ocular benefit composition comprising at least 5 wt % of one or more lipid and/or lipid-derived compounds to deliver an ocular benefit agent to the surface of the eye wherein the composition is applied to a lid margin of the eye.

According to a third aspect of the present invention there is provided an ocular benefit composition comprising at least 5 wt % lipid and/or lipid-derived compounds.

According to a fourth aspect of the present invention there is provided an ocular benefit composition comprising at least 5 wt % of one or more lipid and/or lipid derived compounds for use in the treatment of an eye condition wherein the composition is applied to a lid margin of the eye.

According to a fifth aspect of the present invention there is provided a device for applying an ocular benefit composition to a lid margin of the eye, the device comprising an applicator and a solid mass of the ocular benefit composition; wherein the ocular benefit composition comprises at least 5 wt % of one or more lipid and/or lipid derived compounds.

Preferred features of the first, second, third, fourth and fifth aspects will now be further defined. Any feature of any aspect can be combined with any other feature as appropriate.

In preferred aspects the composition used in the first, second, fourth and fifth aspects is an ocular benefit composition of third aspect.

The present invention is based on the finding that certain lipid and lipid-derived compositions when applied to the lid margin of the eye are spread across the eye through the natural blinking mechanism. This can have a number of beneficial effects.

The ocular benefit composition of the present invention comprises at least 5 wt % lipid of and/or lipid-derived compounds.

By "lipids and/or lipid derived compounds" we mean to include any naturally occurring or synthetically prepared compounds known as lipids and compounds which are structurally similar and/or readily derived there from, for example fatty alcohols.

The lipid and/or lipid derived compounds used in the present invention are suitably not soluble in water.

Lipid and lipid-derived compounds which may be present in the composition of the present invention include oils, fats, waxes, sterols, sterol esters, monoglycerides, diglycerides, triglycerides, phospholipids and fatty alcohols. Other structurally similar compounds may also be present.

Preferably the composition of the present invention comprises at least 10 wt % of lipid and/or lipid derived compounds, preferably at least 20 wt %, more preferably at least 30 wt %, suitably at least 40 wt %, preferably at least 50 wt %, more preferably at least 60 wt %, preferably at least 70 wt %, suitably at least 80 wt %, for example at least 90 wt % or at least 95 wt %.

The compositions used in the present invention may comprise a mixture of two or more different lipids and/or lipid-derived compounds. The above amounts refer to the total of all such compounds present in the composition.

Lipid and lipid-derived compounds suitably for use in the present invention comprise a hydrocarbyl group. The compounds typically include a hydrocarbyl group having at least 6 carbon atoms, preferably at least 8 carbon atoms, more preferably at least 10 carbon atoms.

The hydrocarbyl group may have up to 60 carbon atoms, suitably up to 50 carbon atoms, for example up to 40 carbon atoms.

By hydrocarbyl group we mean to refer to a group which is predominantly hydrocarbon in nature i.e. comprises mostly carbon and hydrogen atoms. The hydrocarbyl group may include one or more non-hydrocarbon substituents, for example hydroxyl or amino groups. However these are preferably less than one for every 6 carbon atoms in the hydrocarbyl group, preferably less than one for every 10 carbon atoms in the hydrocarbyl group The hydrocarbyl group is preferably predominately aliphatic in nature although it may include an aromatic moiety.

The hydrocarbyl group may be saturated, or unsaturated. It may include one or more double bonds.

The hydrocarbyl group may be straight chain or branched.

The hydrocarbyl group is preferably an alkyl or alkenyl group having from 6 to 50, preferably 8 to 40, more preferably from 10 to 36 carbon atoms.

In addition to the hydrocarbyl group, the lipid and lipid-derived compounds will also include one or more functional groups. The type of functional group will depend on the nature of the compound and may be an ester, acid, hydroxyl, phosphonate etc. The types of lipids and lipid-derived compounds and the chemical nature thereof will be known to the person skilled in the art.

The lipid and lipid-derived compounds used in the present invention are typically selected from waxes, fats and oils.

Waxes are compounds which are malleable at room temperature and typically melt at temperatures greater than 45° C.

Fats are a special class of lipids comprising triglycerides of fatty acids that are solid or semi-solid at ambient temperatures.

Oils are lipids that are liquid at ambient temperatures.

Suitable oils include a hydrocarbon chain having between 12 and 30 carbon atoms, preferably between 16 and 24 carbon atoms. The hydrocarbon chain may be saturated, mono unsaturated or polyunsaturated. It may in some embodiments include some further functionality, for example a hydroxyl substituent.

Suitable waxes include a hydrocarbon chain having between 24 and 40 carbon atoms, preferably between 30 and 36 carbon atoms. The hydrocarbon chain may be saturated, monounsaturated or polyunsaturated and may include a functional group for example a hydroxyl residue.

Suitable fats include triglycerides of one or more saturated or unsaturated (including polyunsaturated) fatty acids having 10 to 30, preferably 12 to 24 carbon atoms.

In preferred embodiments the composition of the present invention comprises one or more oils, one or more waxes, and optionally one or more fats.

Examples of waxes suitable for use in the compositions of the present invention include paraffin wax, lanolin, beeswax, jojoba wax, candelilla wax and carnauba wax.

Examples of fats suitable for use in the compositions of the present invention include cocoa butter and shea butter.

Examples of oils suitable for use in the compositions of the present invention include jojoba seed oil, apricot kernel oil, castor seed oil, argan kernel oil, avocado oil, sweet almond oil, hydrogenated castor oil and coconut oil.

Examples of lipid-derived compounds suitable for use in the compositions of the present invention include long chain alcohols, for example octyldodecanol.

The above compounds are merely examples of the types of waxes, oils and fats that can be used in the compositions of the present invention. The selection of other suitable compounds will be within the competence of the person skilled in the art.

Preferably the composition of the present invention comprises at least one wax and at least one oil.

In some embodiments the composition of the present invention comprises at least one wax, at least one oil and at least one fat.

Suitably the composition comprises 5 to 40 wt % waxes, preferably 10 to 25 wt %.

In some preferred embodiments the composition of the present comprises one or more lipid compounds that are naturally found in the tear film.

Polar lipids that are typically present in the tear film include glycerol phospholipids such as phosphatidylcholine, phosphatidylethanolamine, phosphotidylglycerol, phosphatidylinositol, phosphotidylserine, lysophosphatidylcholine, lysophosphatidylethanolamine, sphingolipids such as sphingomyelin, and (O-acyl) ω-hydroxy fatty acids (OAHFAs).

Non-polar lipids typically found in the tear film include wax esters, cholesterol esters, cholesterol, glyceryl esters, steryl esters, hydrocarbons, free sterols, acylglycerols, various diesters and triesters, ceramides and their derivatives, free long-chain fatty acids, hydroxy fatty acids, fatty acid amides. The most abundant of these are the wax esters and the cholesterol esters.

Suitably the composition of the present invention includes one or more of these polar or non-polar lipids.

In some embodiments the composition of the present invention may include one or more polar lipids and one or more non-polar lipids.

Suitably the composition of the present invention is provided in a solid or substantially solid form under ambient conditions. The composition may soften but does not melt at eyelid skin temperature.

Thus the composition of the present invention holds its form and is easy to apply but is readily spread across the surface of the eye on blinking.

Spreading of the composition across the surface of the eye is suitably achieved by a mechanical action due to movement of the eyelid across the eye. This is suitably not due to melting the composition.

Suitably a combination of oils, waxes and optionally fats is carefully selected to provide a composition with a melting point suitable to achieve this effect.

Preferably the composition has a melting point of at least 38° C., more preferably at least 40° C., suitably at least 42° C., preferably at least 44° C. In some embodiments the composition may have a melting point of at least 45° C., at least 46° C., at least 47° C. or at least 48° C.

In some embodiments the composition has a melting point of more than 49° C. or more than 50° C.

Suitably the composition of the present invention has a melting point of between 45° C. and 70° C.

Preferably the composition is a substantially homogenous composition. Suitably it is smooth. Under ambient conditions the composition of the present invention may be provided as a solid mass.

In preferred embodiments the composition of the present invention is not in the form of a gel or paste.

Suitably the composition of the present invention is not an ointment. Suitably it is not a grease.

Suitably the composition of the present invention is provided as a solid block. It is suitably a self-supported solid material.

The composition of the present invention is used to deliver a benefit agent to surface of the eye. In some embodiments the benefit agent may essentially consist of one or more lipid and/or lipid-derived compounds. In some embodiments the composition may include an additional benefit agent.

Preferably the composition of the present invention comprises from 90 to 100 wt % of lipid and/or lipid-derived compounds and from 0 to 10 wt % of one or more additional components. Preferably it comprises from 95 to 100 wt % lipid and/or lipid-derived compounds and from 0 to 5 wt % of one or more additional components.

The additional components may suitably be selected from active pharmaceutical ingredients, diagnostic agents, flavours, fragrances, dyes, pigments, preservatives, photostabilisers, antioxidants and vitamins.

In some embodiments the composition may comprise an active pharmaceutical ingredient. This is suitably present in an amount of from 0.0001 to 2 wt %. However the exact amount of the pharmaceutical active will depend on the particular compound and the condition it is used to treat.

The active pharmaceutical ingredient may be selected from a relief agent for dry eye syndrome, a nerve-reactivating agent, an astringent agent, and anti-inflammatory agent, an anti-bacterial agent, an anti-fungal agent, an anti-viral agent, an anti-allergic agent, an anti-glaucomatous agent, anti-graft rejection agent, a mydriatic agent, an anti-myopia agent, an ocular anaesthetic or a cycloplegic agent.

Examples of suitable active pharmaceutical ingredients which may be used include hydroxyl ethyl cellulose, hydroxyl propyl methyl cellulose, gelatin, polyvinyl alcohol, vitamin A, vitamin B1, vitamin B2, vitamin B6, vitamin B12, vitamin C, vitamin E, vitamin K, camphor, menthol, zinc sulphate, naphazoline (e.g., its HCl salt), tetrahydrozoline, phenylephrine, prednisolone acetate, dexamethasone alcohol, sulphanilamide, neomycin, terramycin, erythromycin, gentamicin, amphotericin B, idoxuridine, antazoline, naphazoline, sodium cromoglycate, pilocarpine, epinephrine, timolol, cyclosporine A, tropicamide, cyclopentolate, pirenzepine and atropine.

In some embodiments the composition may comprise a diagnostic agent, for example a dye compound that can assist examination of the eye. These are suitably included in an amount of from 0.0001 to 1 wt %.

Suitable diagnostic agents include sodium fluoroscene, lissamine green and rose Bengal.

In some embodiments the benefit agent may be a compound which provides a cosmetic effect, for example enhanced whiteness, increased sparkle or improved moistness. Examples of such compounds include decongestants/astringents, naphazoline, hydrochloride, xylometazoline, antazoline, zinc sulphate and witch hazel.

The composition of the present invention may further comprise a skin protection agent. Suitable skin protection agents include petrolatum, mineral oil, lanolin, dimethicone, cocoa seed butter and allantoin.

Skin protection agents are typically included in an amount of up to 5 wt %, for example in an amount of from 0.01 to 2 wt %, suitably from 0.1 to 1 wt %.

The composition of the present invention may include a flavour and/or fragrance. Suitably these are present in an amount of up to 5 wt %, for example in an amount of from 0.01 to 2 wt %, suitably from 0.1 to 1 wt %. Suitable flavours and fragrances include linalool, benzyl benzoate, citral, geraniol, citronellol, saccharin and sodium saccharin.

The composition of the present invention may further comprise an antioxidant. These are typically present in an amount of up to 1 wt %, for example in an amount of from 0.01 to 0.1 wt %.

Suitable antioxidants will be known to the person skilled in the art and include tocopheryl acetate, BHT, ascorbyl palmitate and tocopherol.

The composition of the present invention may comprise a preservative. Preservatives are suitably present in an amount of from up to 1 wt %, preferably in an amount of from 0.01 to 0.5 wt %. Suitable preservatives are known to the person skilled in the art and include parabens.

The composition of the present invention may comprise one or more vitamins. These may be present in an amount of up to 5 wt % and are typically present in an amount of from 0.001 to 1 wt %, for example 0.01 to 0.5 wt %.

Suitable vitamins for inclusion in the composition of the present invention are fat-soluble vitamins for example vitamin A, D, E and K.

The ocular benefit composition of the present invention is preferably not an aqueous composition.

Suitably the composition used in the present invention comprises less than 50 wt % water, preferably less than 30 wt %, preferably less than 20 wt %, more preferably less than 10 wt %. Preferably the composition of the present invention comprises less than 5 wt % water, suitably less than 3 wt %, preferably less than 2 wt %, more preferably less than 1 wt %. In some embodiments the composition of the present invention comprises less than 0.5 wt % water, suitably less than 0.1 wt %.

In some preferred embodiments water is not added as an ingredient when preparing the compositions for use in the present invention. Small amounts of water may be present as the ingredients are not dried. However in some embodiments none of the ingredients is aqueous based.

In some embodiments in which the composition comprises an active pharmaceutical ingredient that is water soluble, small amounts of water may be included, for example by 5 wt %. This is to assist dissolution and delivery of the active agent.

In some embodiments the composition of the present invention is a cosmetic composition.

In some embodiments the composition may be an eyeliner composition. Eyeliners are used by wearers to enhance definition of the eyes and are sometimes applied to the lid margins.

When the composition of the present invention is an eyeliner composition it suitably includes one or more pigments. Suitable pigments will be known to the person skilled in the art and include black iron oxides, titanium dioxide and prussian blue.

Pigments are typically included in an amount of up to 1 wt %. The selection of an appropriate concentration of pigment is within the competence of the person skilled in the art.

When the eyeliner is used the lipids present in the composition are spread across the eye on blinking. Suitably the pigment (which will be present in small amounts) remains substantially on the lid margin.

The composition of the present invention may comprise petrolatum. However in preferred embodiments this is not present as a major ingredient.

Preferably the composition of the present invention comprises less than 50 wt % petrolatum, preferably less than 40 wt %, more preferably less than 30 wt %, suitably less than 20 wt %, for example less than 10 wt %.

In some embodiments the composition comprises less than 2 wt % or less than 1 wt %.

In some embodiments the composition of the present invention does not contain a calcium salt.

The composition of the present invention may comprise naturally occurring lipid and/or lipid derived compounds and/or it may comprise synthetically prepared lipid and/or lipid derived compounds.

In preferred embodiments at least 10 wt % of the lipid and/or lipid derived compounds present in the composition of the present invention are obtained from natural sources, preferably at least 20 wt %, suitably at least 30 wt %, for example at least 40 wt %.

In some embodiments at least 50 wt % of the lipid and/or lipid derived compounds present in the composition are obtained from natural sources, suitably at least 60 wt %, for example at least 70 wt %, at least 80 wt % or at least 90 wt % or at least 95 wt %.

In some embodiments the composition of the present invention is an ocular comfort composition.

Suitably in such embodiments the composition consists essentially of lipid and/or lipid-derived compounds. It may comprise minor amounts of excipients such as fragrances and preservatives but these are typically present in an amount of less than 5 wt %.

Such compositions typically do not include an active pharmaceutical ingredient.

In such embodiments of the present invention the benefit agent is the lipid and/or lipid derived compounds.

The present invention may suitably provide an ocular comfort composition comprising at least 5 wt % of one or more lipid and/or lipid derived compounds for use in the treatment of one or more conditions that cause ocular discomfort, for example the conditions known as dry eye.

Suitably in such embodiments the ocular comfort composition is an ocular benefit compound as previously defined herein. Preferably it comprises at least 90 wt % lipid and/or lipid derived compounds.

The present invention may suitably provide a method of relieving one or more symptoms ocular discomfort, for example those caused by the condition known as dry eye, the method comprising applying to a lid margin of the eye an ocular comfort composition comprising at least 5 wt % of one or more lipid and/or lipid derived compounds.

Suitably ocular comfort compositions of the present invention may help relieve discomfort caused by the wearing of contact lenses.

One of the major reasons why people discontinue with the use of contact lenses is due to ocular discomfort and/or irritation. In particular many wearers find that their contact lenses become less comfortable the longer they wear them. Thus often people who need to wear contact lenses all day find that their eyes are uncomfortable by the evening.

The composition of the present invention may help reduce the discomfort caused by wearing contact lenses and thus may prolong the time for which contact lenses can be tolerated. This in turn should reduce the number of people who discontinue using contact lenses due to discomfort.

Thus the invention may provide the use of an ocular benefit composition comprising at least 5 wt % of one or more lipid and/or lipid-derived compounds to relieve discomfort caused by wearing contact lenses.

Suitably the ocular benefit composition is as previously described herein.

In some embodiments the ocular benefit composition of the present invention is an ocular pharmaceutical preparation.

In such embodiments the preparation suitably comprises one or more active pharmaceutical compounds. The ocular pharmaceutical preparation is suitably an ocular benefit composition as previously defined herein. Suitable active pharmaceutical ingredients are as previously described herein.

Suitably the present invention provides an ocular benefit composition as defined herein comprising an active pharmaceutical ingredient for use in the treatment of an ocular disease.

The ocular pharmaceutical preparation of the present invention may be used to treat one or more conditions selected from blepharitis, conjunctivitis, corneal epithelial erosions, dry eyes, glaucoma, irritation from hayfever, keratitis, myopia, other ocular infections and other ocular inflammations.

The present invention is particularly effective at delivering active pharmaceutical ingredients to the surface of the eye.

The present invention may provide a method of treating an ocular disease, the method comprising contacting a lid margin of the eye with an ocular pharmaceutical preparation comprising at least 5 wt % lipid and/or lipid-derived compounds and an active pharmaceutical ingredient.

The compositions and method of the present invention may help relieve symptoms of discomfort caused by an ocular disease as well as delivering pharmaceutical agents which tackle the underlying cause of the disease.

In some embodiments the ocular benefit composition of the present invention is a cosmetic composition.

Such cosmetic compositions include one or more ingredients which alter the appearance of the eye.

In some embodiments the composition is an eyeliner composition and it further comprises one or more pigments or dyes.

The provision of such eyeliner compositions would enable sufferers of a variety of eye conditions (for example dry eye) to wear this and other eye make-up. This would otherwise not be possible as their eyes would water or they would want to rub them. Eye treatment compositions of the prior art are often not compatible with wearing make-up.

In some embodiments the composition comprises one or more ingredients which enhances the sparkle, brightness or whiteness of the eye.

In the methods and uses of the present invention the ocular benefit composition is applied to a lid margin of the eye. It may be applied to one or both of the lid margins. It may be applied to a portion of the lid margin or across the length of the or each lid margin.

Preferably the composition is applied to the lower lid margin.

In some embodiments it is applied to the lower lid margin and the upper lid margin.

In some embodiments it is applied only to the lower lid margin.

In some preferred embodiments the composition is applied to the inner (or "posterior") lid margin.

An advantage of applying the composition to the lid margin is that it can be delivered across the surface of the eye by the natural blinking mechanism.

A further advantage is that the method of the present invention does not make the skin around the eyes shiny or sticky.

Advantageously, the composition of the present invention is suitably stable under normal transport and storage temperatures. Suitably the composition is stable when stored at temperatures of from 0° C. to 35° C. for periods of up to 1 week, suitably up to 1 month, preferably up to 6 months.

The composition may be stable when stored at a temperature of from 0° C. to 35° C. for one year or more.

By stable we mean that the composition does not chemically or physically degrade, during the storage period. Suitably its appearance remains the same during the storage period, for example it does not discolour.

A considerable and surprising advantage of the present invention is the long lasting efficacy of the compositions used in the present invention.

For example in the case of ocular comfort compositions the inventors have surprisingly found that the relief from the symptoms of dry eye lasts much longer than for methods of the prior art.

One major disadvantage of the prior art treatments for dry eyes is that they must be frequently applied throughout the day. Long lasting ointments are available but these impair vision. The compositions of the present invention provide long lasting relief without significantly impairing vision.

Thus the present invention suitably provides an ocular comfort composition as defined herein which maintains ocular comfort for a period of at least 30 minutes, preferably at least 60 minutes, for example at least 90 minutes.

In some embodiments the composition maintains comfort for at least 2 hours, suitably for at least 3 hours or at least 4 hours.

The fourth aspect of the present invention may provide an ocular benefit composition comprising at least 5 wt % of one or more lipid and/or lipid derived compounds for use in the treatment of an eye condition wherein the composition is applied to a lid margin of the eye and wherein the composition is applied to the eye no more than 10 times in a 24 hour period.

The eye condition is suitably as previously defined herein.

Suitably the composition is applied to the eye no more than 8 times in a 24 hour period, preferably no more than 6 times, more preferably no more than 4 times.

Suitably the present invention provides an ocular benefit composition comprising at least 5 wt % of one or more lipid and/or lipid derived compounds for use in the treatment of an eye condition wherein the composition is applied to a lid margin of the eye and wherein the composition is applied to the eye no more than 5 times in a 12 hour period.

Suitably it is applied to the eye no more than 3 times in a 12 hour period, preferably no more than twice in a 12 hour period.

In the method of the present invention the ocular benefit composition is applied to a lid margin of the eye. Suitably it is applied along the line of the meibomium glands.

Suitably the majority (at least 50%, preferably at least 70%) of the composition that is applied is delivered to the lid margin. The composition suitably does not smear around the eye, or drip down the face.

Suitably about 0.1 to 0.2 g of the composition is delivered to the lid margin on each application.

The composition is suitably deposited on the lid margin in a thin layer on application in a manner similar to application of a lipstick or eyeliner.

In some embodiments the lid margin may be polished prior to application of the ocular benefit composition. Polishing of the lid margin may suitably be achieved by rubbing the finger or a tool over the lid margin. This will help remove any debris or grease on the margin allowing improved delivery of the ocular benefit composition to the lid margin.

Polishing the lid margin and thus massaging and stimulating the meibomian glands will also help open the orifices of the meibomian glands, removing epithelial cells and preventing blocking.

The composition may be applied to the lid margin by any suitable means. Suitably the composition is applied by contacting a solid source of the composition with the lid margin. Suitably a solid source of the composition is rubbed along the lid margin.

The present inventors have developed a device to facilitate easy and accurate application of the composition to the lid margin.

Preferably the ocular benefit composition is applied to the lid margin using a device of the fifth aspect.

Such a device comprises an applicator and a mass of the ocular benefit composition. The ocular benefit composition in the device is suitably provided in solid form. It is provided as a shaped mass which under ambient conditions retains its shape.

The ocular benefit composition included in the device of the fifth aspect is suitably as defined in relation to the third aspect.

The applicator and the ocular benefit composition form a single component of the device.

The applicator is configured to enable a user to easily handle the device.

Such a device comprises an applicator and a mass of the ocular benefit composition. This means that a user does not touch the ocular benefit composition during normal handling of the device. This is advantageous as it prevents the composition melting or leaving a residue on the hands of the user.

Suitably the applicator partly contains or surrounds the mass of the ocular benefit agent.

Suitably the applicator is an elongate member. Preferably it is tubular. It may be of any suitable cross-section. Most preferably it is cylindrical.

Preferably the applicator is tubular and the ocular benefit composition extends from one end of the applicator. In some preferred embodiments the mass of ocular benefit composition is elongate.

Suitably the applicator has a substantially hollow core wherein the elongate mass of ocular benefit agent is located within the core and extends from one end of the core.

In preferred embodiments the mass of ocular benefit composition is in elongate form and is surrounded by the applicator along most of its length.

The applicator may be made from any suitable material. Such materials include plastics, metal and wood.

In some embodiments the benefit composition may extend form each end of the applicator. Preferably it extends from only one end of the applicator.

In some embodiments the ocular benefit composition extends from one end of the applicator and the other end is provided with means for polishing the lid margin.

The means for polishing the lid margin is suitably a shaped body, suitably a smooth rounded body, for example of a rubber or plastics material.

Suitably a portion of the mass of ocular benefit composition extends from an end of the applicator and the remainder is contained within the applicator body (e.g. a hollow tubular member).

The device may be provided with means for advancing the mass of ocular benefit composition. Such means suitably facilitates movement of the mass within the body of the applicator towards the open end such that new material is exposed as the composition is consumed. Such means will be known to the person skilled in the art and include means for pushing and/or twisting.

The mass of ocular benefit composition is suitably shaped at the end which extends from the applicator to facilitate application to the lid margin. It may suitably have a rounded tip. Preferably the tip has a maximum cross-sectional dimension of less than 5 mm, for example it has a diameter of 1-2 mm.

In some embodiments the applicator may be made from wood and the device may be in the form of a traditional pencil wherein the ocular benefit composition runs through the centre of the wood.

In some embodiments the ocular benefit composition may be provided in a plurality of small cartridges which are inserted into the applicator in the manner of a cartridge pencil. Such embodiments may facilitate the provision of a single does of benefit agent per cartridge, or a daily dose, for example. This may be advantageous for embodiments in which the composition contains an active pharmaceutical ingredient, to prevent overdosing.

In some preferred embodiments the applicator is made from a plastics or metallic material. Suitably the applicator is a tubular member. Suitably it is cylindrical. One end of the applicator suitably has an aperture through which the mass of ocular benefit agent extends. The mass of ocular benefit agent in such embodiments is also preferably tubular (especially cylindrical). The mass of ocular benefit composition is suitably connected to advancing means provided at the other end of the applicator.

Devices of this type may have a structure which is in some ways similar to a twist to advance pencil or an advancing pencil and in some ways similar to a lipstick or lip balm product.

In preferred embodiments the device further includes a lid. The lid covers the exposed end of the ocular benefit composition preventing it from collecting dirt or dust.

In some embodiments the lid may be provided with a mirror at the end thereof. The lid is suitably shaped to coordinate with the applicator.

The dimensions of the applicator are suitably selected to facilitate ease of holding and application of the composition to the lid margin of the eye.

The applicator may be provided with a textured surface for ease of gripping.

The length of the applicator is preferably at least 3 cm, preferably at least 5 cm. Suitably the length of the applicator is up to 20 cm, suitably up to 15 cm.

Preferably the applicator is from 6 to 12 cm in length, preferably from 7 to 10 cm.

In some preferred embodiments the applicator is cylindrical. It suitably has a diameter of at least 5 mm. It suitably has a diameter of up to 20 mm. Preferably the applicator has a diameter of from 8 to 15 mm.

The mass of ocular benefit composition is suitably substantially cylindrical in shape. It suitably has a diameter of less than 10 mm, preferably less than 5 mm, for example 2 to 4 mm. It suitably narrows at the tip.

The invention will now be further described with reference to the following non-limiting examples.

EXAMPLE 1

An ocular comfort composition according to the present invention was prepared comprising the following components:

20% jojoba wax
24% shea butter
8% cocoa butter
48% apricot kernel oil

EXAMPLE 2

The composition of example 1 was applied to the lower lid margin of the eye and the eye was photographed before application and 5 minutes after application.

Figure 2:
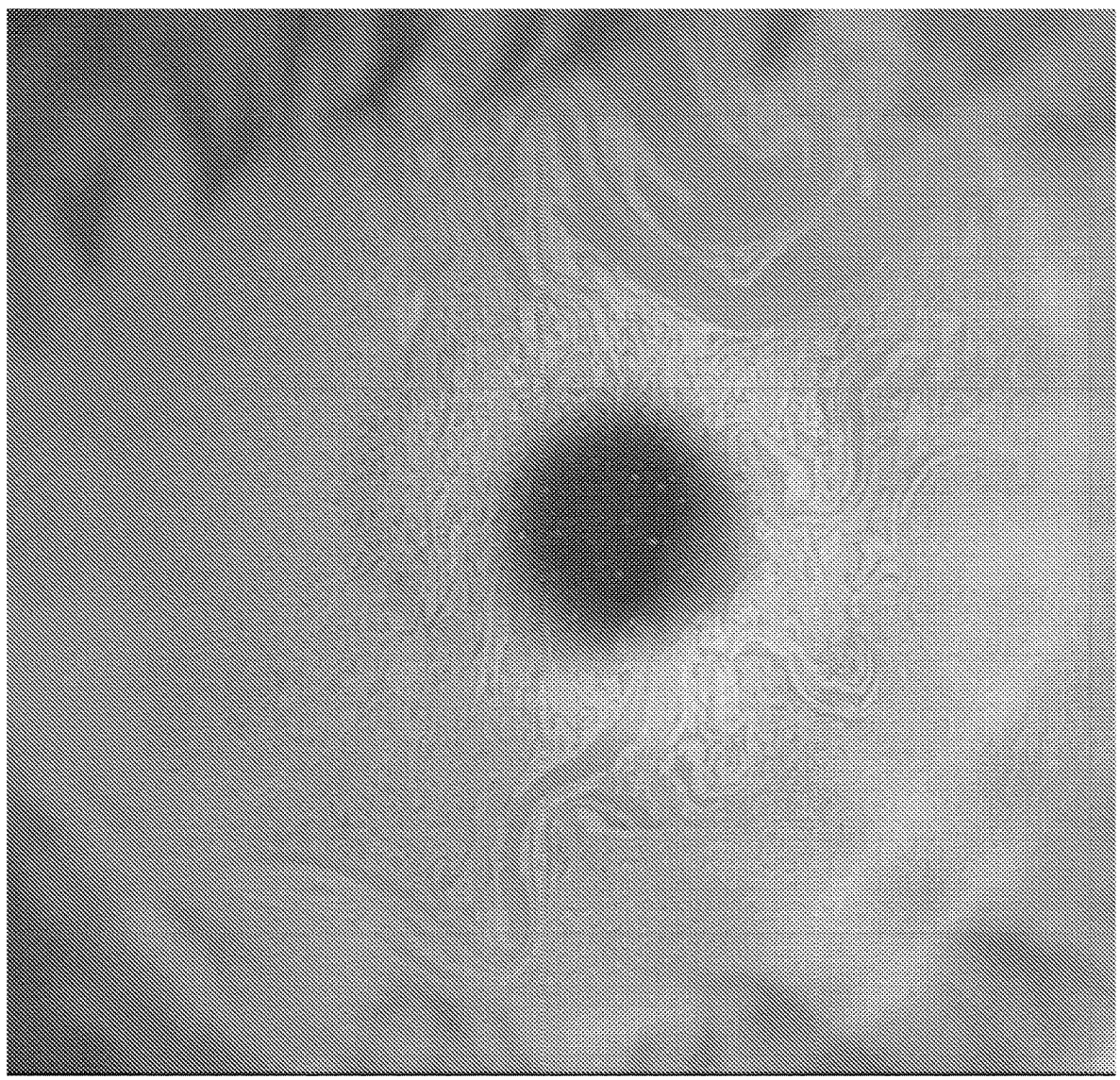
FIG. 2 shows the treated eye 5 minutes after application at 16 x magnifaction.
Figure 3:
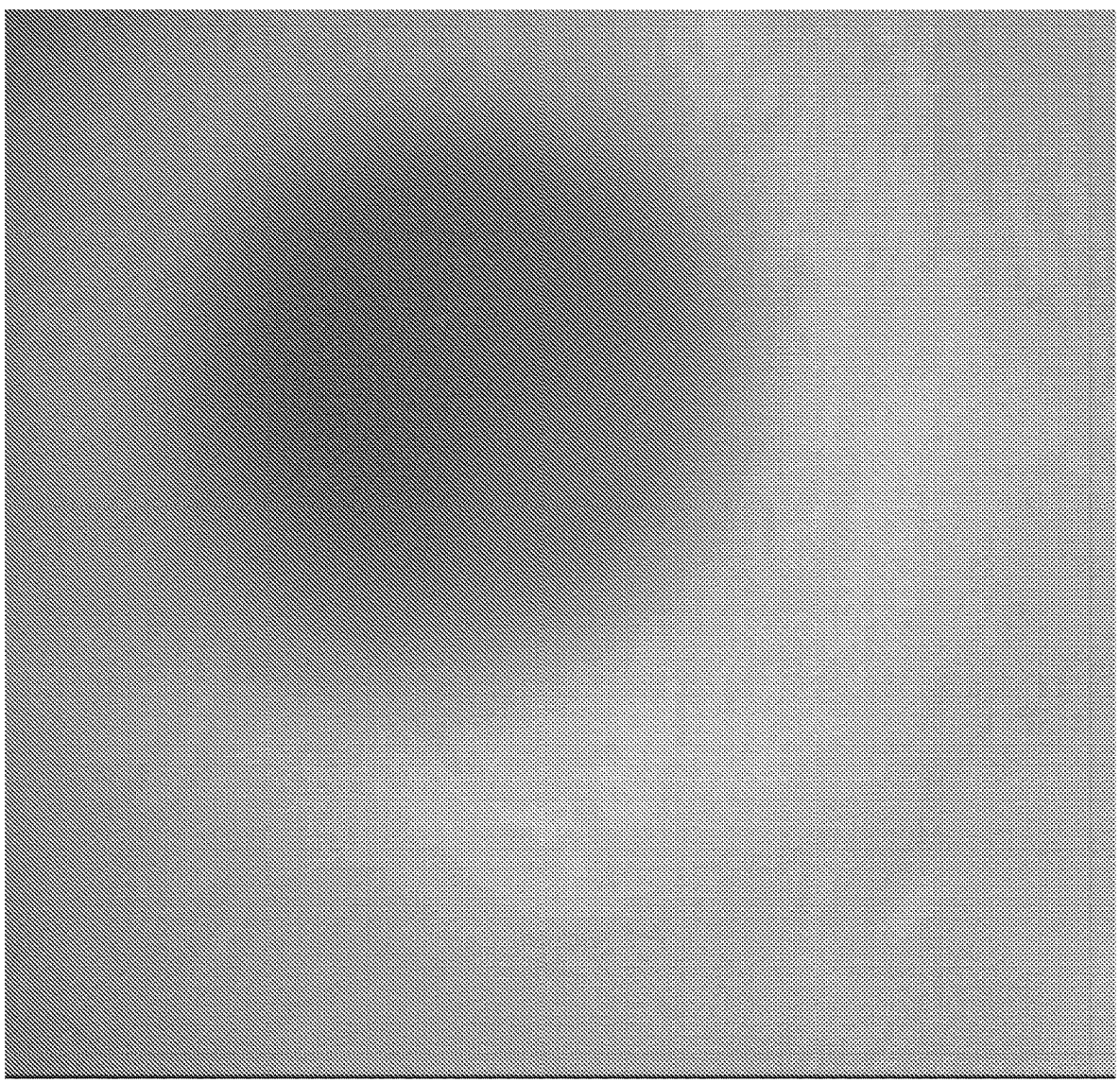
FIG. 3 shows the untreated eye at 40 x magnification.
Figure 4:
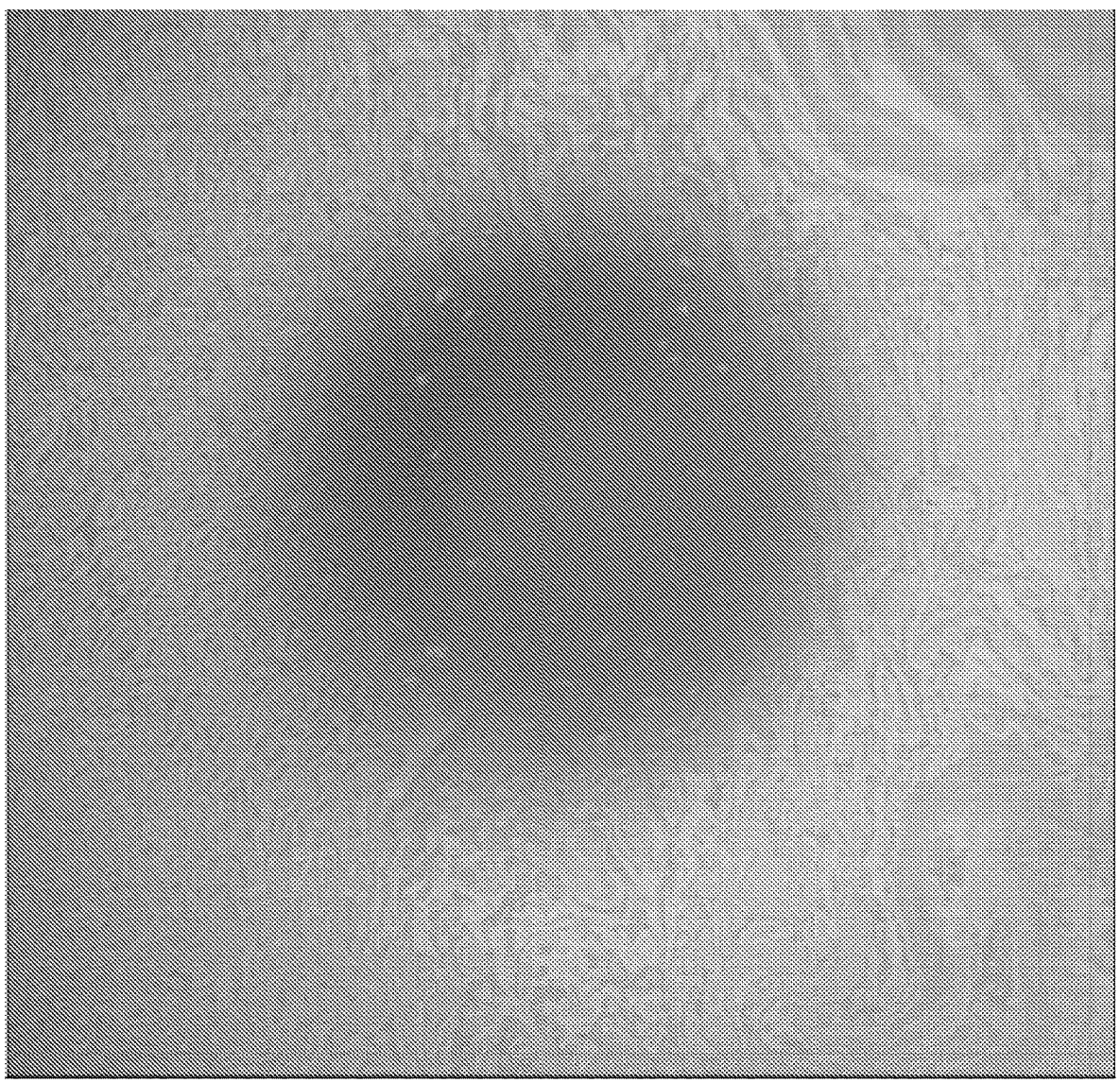
FIG. 4 shows the treated eye 5 minutes after application at 40 x magnification.

FIG. 1 shows the untreated eye at 16× magnification.
FIG. 2 shows the treated eye 5 minutes after application at 16× magnification.
FIG. 3 shows the untreated eye at 40× magnification.
FIG. 4 shows the treated eye 5 minutes after application at 40× magnification.

EXAMPLE 3

A composition according to the invention was applied to the lower lid margin of an eye. Optrex® eye spray was dosed according to standard instructions into the other eye.

Figure 5:
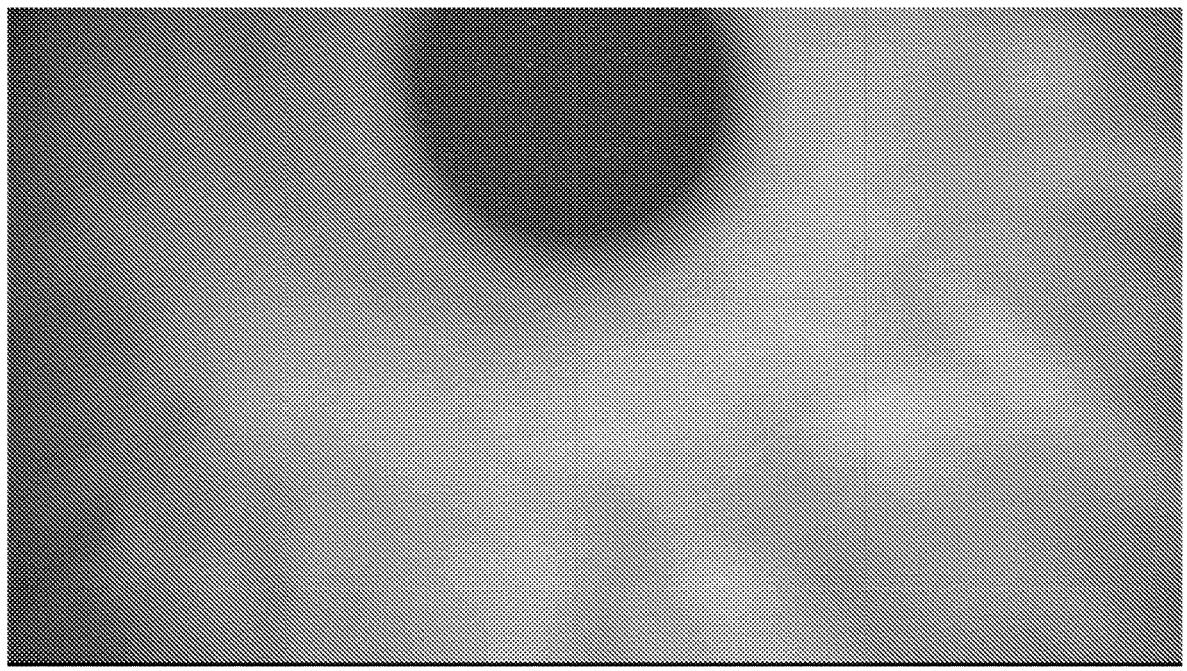
FIG. 5 shows an eye treated with Optrex spray 5 hours after application.
Figure 6:
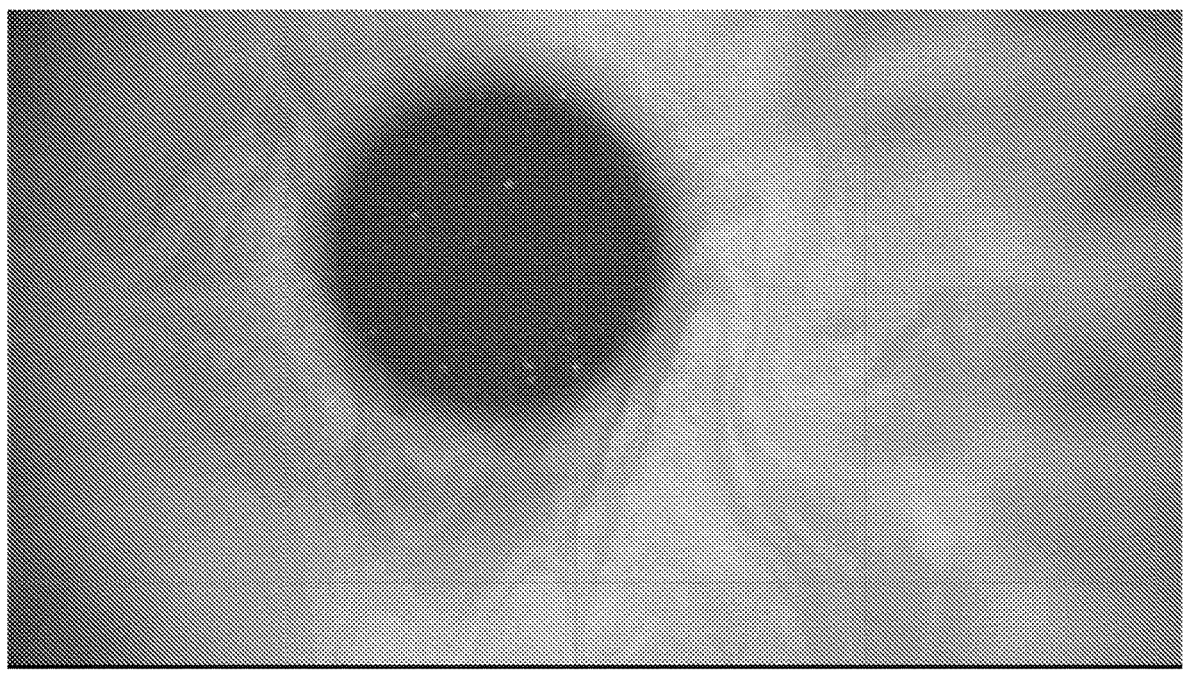
FIG. 6 shows an eye treated with the composition of the invention, 5 hours after application.

FIG. 5 shows an eye treated with Optrex spray 5 hours after application.
FIG. 6 shows an eye treated with the composition of the invention, 5 hours after application.

FIGS. 1 to 6 clearly show how lipids are spread across the surface of the eye in the present invention and that the effect is long lasting.

EXAMPLE 4

Figure 7:
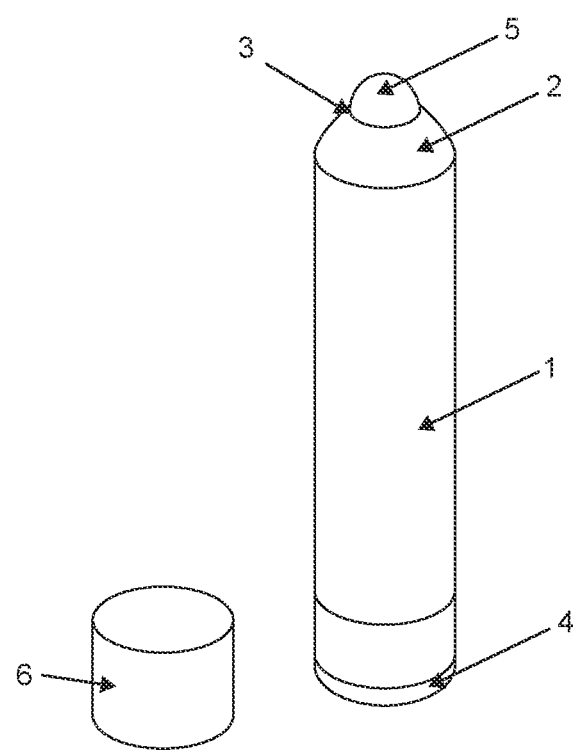
FIG. 7 shows an example device of the present invention.

An example device of the present invention is shown in FIG. 7.

The device comprises a tubular body 1 which tapers at one end 2 to an opening 3. At the other end the tubular body is closed by rotating means 4. A stick of ocular benefit composition 5 protrudes from the opening and is rounded at the end. The other end of the stick of composition is held within the tubular body and may be advanced by turning the rotating means 4. The device is provided with a removable lid 6.

EXAMPLE 5

The thickness of the lipid layer is known to be reduced in patients with dry eye, increasing the rate to tear film evaporation (Blackie et al, Cornea. 2009 August; 28(7):789-94. 2009). Lipid layer thickness can be measured using the TearScience Lipiview interferometer. This instrument can measure lipid layer thicknesses between 0 nm and 100 nm.

Three subjects, each with a healthy tear film, were assessed with the Lipiview instrument prior to and following application of the ocular comfort composition of example 1. The composition was applied to the lower lid margin of both eyes.

Figure 8:
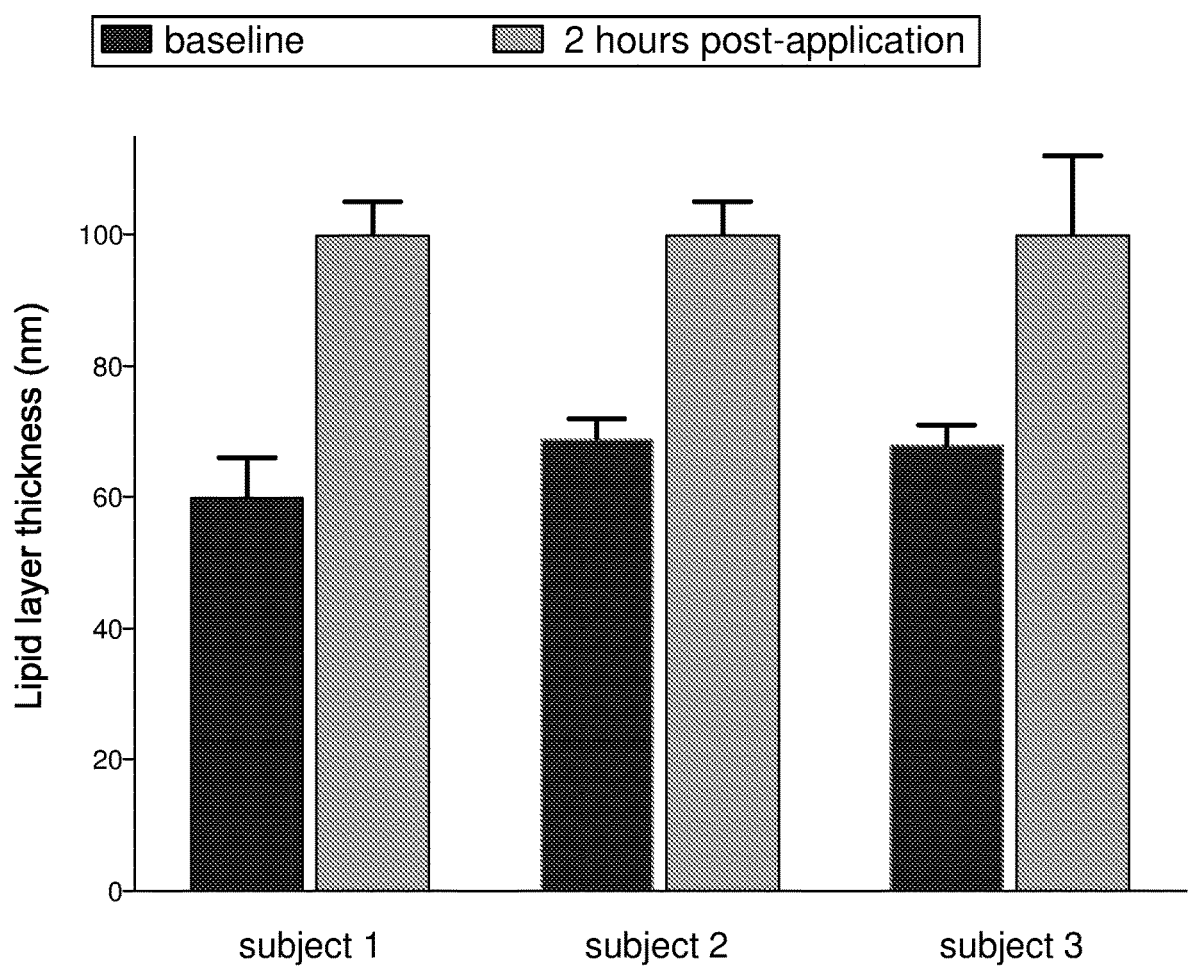
FIG. 8 highlights the increase in lipid layer thickness 2 hours after application.

The Lipiview instrument highlighted a rapid thickening of the lipid layer, in both eyes, for all three subjects. FIG. 8 highlights the increase in lipid layer thickness 2 hours after application.

Figure 9A:
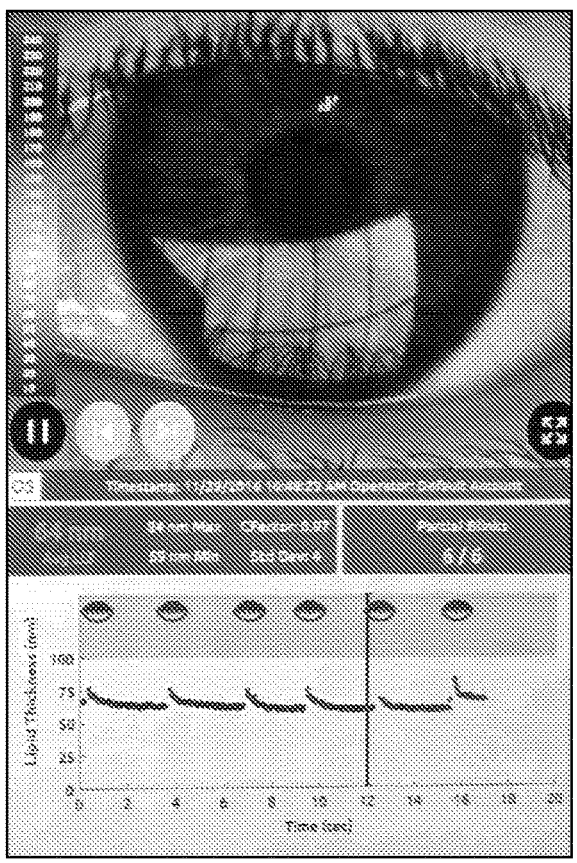
FIG. 9A shows the baseline lipid layer thickness for a first individual.
Figure 9B:
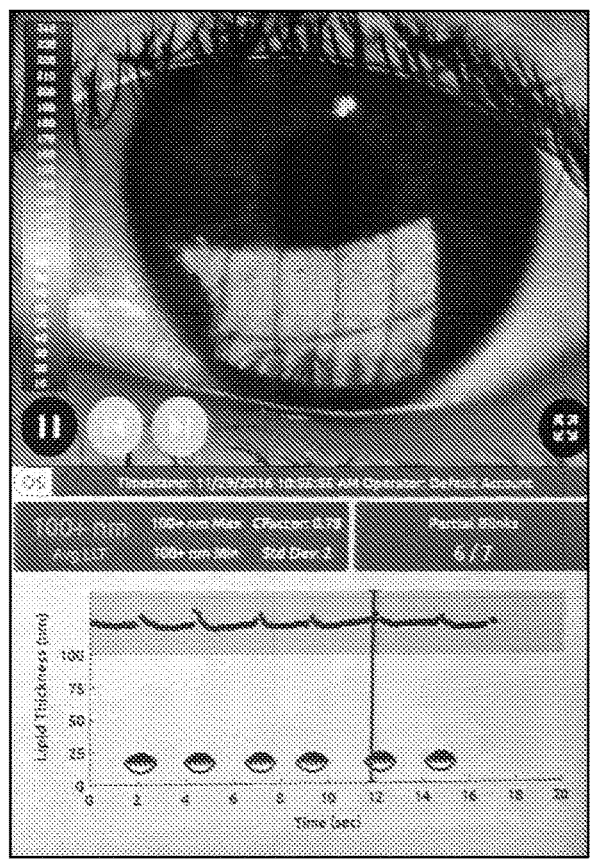
FIG. 9B shows the thickness for the same individual after 5 minutes.

FIG. 9A shows the baseline lipid layer thickness for a first individual and FIG. 9B shows the thickness for the same individual after 5 minutes.

Figure 9C:
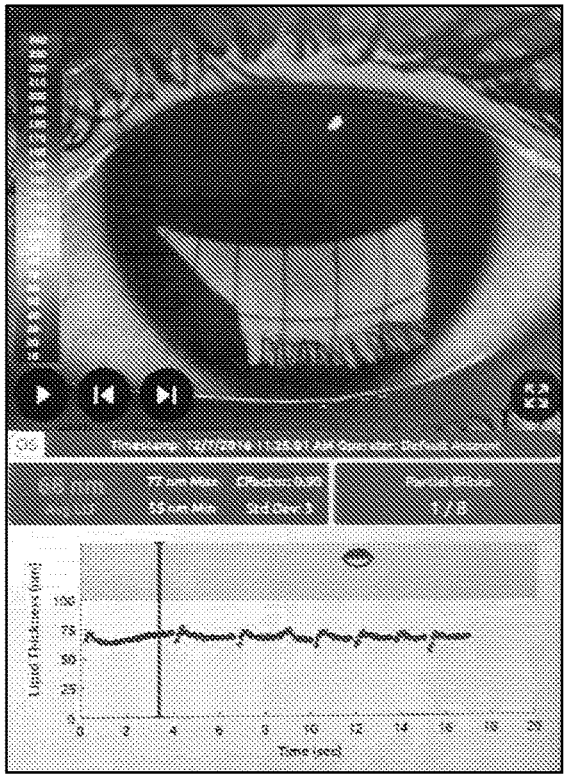
FIG. 9C shows the baseline lipid layer thickness for a second individual.
Figure 9D:
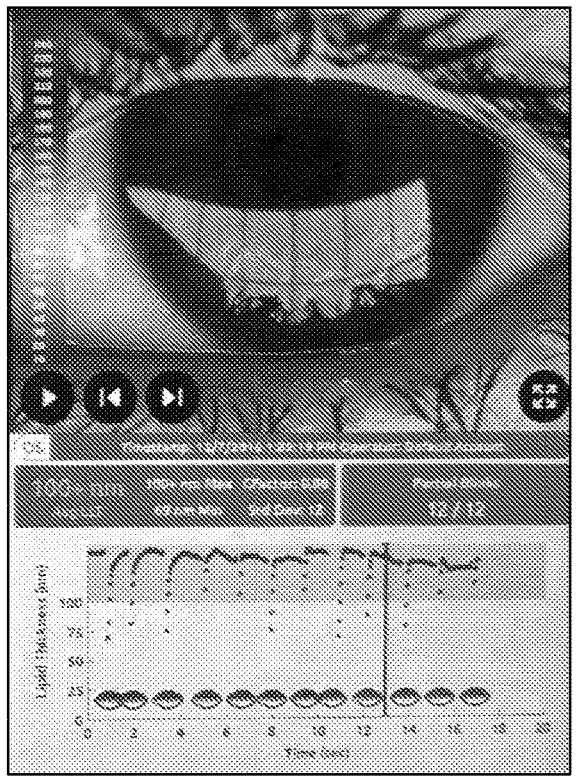
FIG. 9D shows the thickness for the same individual after 2 hours.

FIG. 9C shows the baseline lipid layer thickness for a second individual and FIG. 9D shows the thickness for the same individual after 2 hours.

Application of the composition onto the lid margins resulted in a thickening of the lipid layer of the tear film, which was sustained for a number of hours after application. These findings highlight the gradual release of lipid product from the lid margin into the tear film.

The invention claimed is:

1. A method for delivering a benefit agent to the surface of the eye, the method comprising applying an ocular benefit composition to a lid margin of the eye wherein the ocular benefit composition comprises at least 95 wt % of one or more lipid and/or lipid derived compounds, wherein shea butter is present in a concentration of at least 10 wt % of the composition
   wherein the composition has a melting point of at least 45° C. and is a self-supported solid material,
   wherein the lipid and/or lipid derived compounds are selected from the group consisting of oils, fats, waxes, sterols, sterol esters, monoglycerides, phospholipids and fatty alcohols,
   wherein the composition comprises one or more waxes and one or more oils, and
   wherein one or more oils are selected from the group consisting of jojoba seed oil, apricot kernel oil, castor seed oil, argan kernel oil, avocado oil, sweet almond oil, hydrogenated castor oil and coconut oil.

2. A method according to claim 1 wherein the ocular benefit composition comprises one or more waxes, one or more oils and one or more fats.

3. A method according to claim 1 wherein the ocular benefit composition is provided in solid form.

4. A method according to claim 1 wherein the ocular benefit composition is a comfort composition which relieves one or more symptoms of ocular discomfort.

5. A method according to claim 1 wherein the ocular benefit composition is a pharmaceutical preparation which comprises one or more active pharmaceutical compounds.

6. A method according to claim 1 wherein the ocular benefit composition is a cosmetic composition which comprises one or more ingredients which alter the appearance of the eye.

* * * * *